(12) United States Patent
Song (10) Patent No.: US 10,245,158 B2
(45) Date of Patent: Apr. 2, 2019

(54) CAGE FOR SPINAL INTERBODY FUSION (71) Applicant: Kwang Yong Song, Gyeonggi-do (KR)

(72) Inventor: Kwang Yong Song, Gyeonggi-do (KR)

( * ) Notice: Subject to any disclaimer, the term of this patent is extended or adjusted under 35 U.S.C. 154(b) by 0 days.

(21) Appl. No.: 15/740,953

(22) PCT Filed: May 3, 2016

(86) PCT No.: PCT/KR2016/004676
§ 371 (c)(1),
(2) Date: Dec. 29, 2017

(87) PCT Pub. No.: WO2017/003082
PCT Pub. Date: Jan. 5, 2017

(65) Prior Publication Data
US 2018/0185162 A1    Jul. 5, 2018

(30) Foreign Application Priority Data

Jun. 29, 2015 (KR) .................. 10-2015-0091812

(51) Int. Cl.
*A61F 2/44* (2006.01)
*A61L 27/06* (2006.01)
(Continued)

(52) U.S. Cl.
CPC .............. *A61F 2/447* (2013.01); *A61F 2/44* (2013.01); *A61F 2/4611* (2013.01); *A61L 27/06* (2013.01); *A61L 27/56* (2013.01); *A61F 2002/3008* (2013.01); *A61F 2002/3092* (2013.01); *A61F 2002/30125* (2013.01); *A61F 2002/30268* (2013.01); *A61F 2002/30271* (2013.01); *A61F 2002/30622* (2013.01); *A61F 2002/30777* (2013.01); *A61F 2002/30789* (2013.01);
(Continued)

(58) Field of Classification Search
CPC .............................................. A61F 2/44–2/447
USPC .......................................... 623/17.11–17.16
See application file for complete search history.

(56) References Cited

U.S. PATENT DOCUMENTS

2007/0250167 A1 * 10/2007 Bray ..................... A61F 2/4455
623/17.11
2008/0288076 A1 * 11/2008 Soo ...................... A61F 2/30771
623/17.16
(Continued)

FOREIGN PATENT DOCUMENTS

KR    20130032575 A  *  4/2013  ............... A61F 2/44

*Primary Examiner* — Nicholas J Plionis
(74) *Attorney, Agent, or Firm* — TIPS Group (57) ABSTRACT

One embodiment of the present invention provides a cage for spinal interbody fusion, which has sufficient durability and allows for bone fusion with a bone implanted to the anterior disk as well as fusion between vertebrae, thereby achieving a more stable bone fusion. The cage for spinal interbody fusion according to the embodiment of the present invention comprises a cage body and a tip which is formed to extend from the cage body and have a predetermined curvature. Further, the cage body has a cavity part which is formed to penetrate from the top surface to the bottom surface of the cage body with a projection part having a plurality of projections formed on the top surface and the bottom surface, and at least one perforation part, which is perforated from the side surface adjacent to the top surface or the bottom surface to the direction of the cavity part, and is located in the anterior direction of the cavity part.

10 Claims, 6 Drawing Sheets

(51) Int. Cl.
*A61F 2/46* (2006.01)
*A61L 27/56* (2006.01)
*A61F 2/30* (2006.01)

(52) U.S. Cl.
CPC ............... *A61F 2002/30904* (2013.01); *A61F 2002/4475* (2013.01); *A61F 2310/00023* (2013.01); *A61F 2310/00029* (2013.01); *A61F 2310/00059* (2013.01); *A61L 2430/38* (2013.01)

(56) References Cited

U.S. PATENT DOCUMENTS

| | | | | |
|---|---|---|---|---|
| 2011/0112642 | A1* | 5/2011 | Tohmeh | A61F 2/4455 623/17.11 |
| 2013/0076157 | A1* | 3/2013 | Stein | A61F 2/442 307/116 |
| 2016/0296344 | A1* | 10/2016 | Greenhalgh | A61F 2/4601 |

* cited by examiner

CAGE FOR SPINAL INTERBODY FUSION

TECHNICAL FIELD

The present invention relates to a cage for spinal interbody fusion, and more specifically to a cage for spinal interbody fusion which has sufficient durability and allows for quick and stable fusion between vertebrae through an anterior penetration part thereof, as well as fusion with bones implanted at a front of a disk, thereby resulting in an excellent bone fusion.

BACKGROUND ART

A spine consists of vertebrae and intervertebral disks which are known as disks and are located between the vertebrae. Due to various causes such as diseases or accidents, spinal nerves are pressed by structures of a human body, thereby causing neurological disorders. In such a case, surgical treatment is required. In a case of vertebral fusion among the surgical treatment methods, spinal interbody fusion, in which a disk is removed and a cage, which is an artificial correction material, is inserted between the vertebrae to fuse the vertebrae, has been commonly and largely performed in recent years. In such an operation, it is important to increase a bone connection between the implanted cage and the vertebrae.

In general, the above-described spinal interbody fusion is performed by incising a back side of the human body, implanting a bone into a space between the disks, which is formed by removing the disks to the back of the vertebra, and then inserting a cage for spinal interbody fusion to cause upper and lower vertebrae to be fused with each other. A cage for anterior lumbar interbody fusion developed for this purpose causes not only the upper and lower vertebrae to be fused with each other through bone chips or bone substitutes such as an artificial bone or autogenous bone filled in an internal space thereof, but also the bones implanted in the anterior region of the disk to be fused with each other through an anterior penetration part formed therein.

As such, the cage for spinal interbody fusion serves to constantly maintain the space between the intervertebral disks until a formation of the bones is completed. Therefore, a function of quickly and stably inducing a growth of bone cells while having sufficient durability is required for the cage for spinal interbody fusion.

Korean Patent Registration No. 10-1352820 discloses an expandable cage for lumbar interbody fusion (hereinafter, referred to as 'prior art 1'). The expandable cage for lumbar interbody fusion includes: a cage body including an upper support part for supporting a vertebra located on an upper side of the lumbar interbody, a lower support part for supporting a vertebra located at a lower side of the lumbar interbody, and a connecting part for connecting ends of the upper and lower support parts; and a sliding member slidably mounted between the upper support part and the lower support part so as to increase or decrease a gap between the upper and lower support parts.

DISCLOSURE

Technical Problem

The above-described prior art 1 has a first structural problem that, since the anterior part of the cage body which faces the front of the vertebra during insertion of the cage is formed in a simple planar shape, bones are not fused with each other at a portion adjacent to an anterior portion of the disk, in which a lot of bone implantations are substantially carried out.

Further, the above-described prior art 1 has a second problem that, since inner surfaces of portions which are perforated in a predetermined shape at side surfaces of the cage are simply formed perpendicularly to an outer surface, if a ratio of the perforated portion is large, the durability is deteriorated, and if the ratio thereof is small, a growth rate of the bone is reduced.

Technical objects of the present invention are not particularly limited to those described above, and other technical objects not described herein will also be clearly understood from the following description by a person who has a common knowledge in the technical field to which the invention pertains.

Technical Solution

It is an object of the present invention to provide a cage for spinal interbody fusion which has sufficient durability and allows for quick and stable fusion between vertebrae through an anterior penetration part thereof, as well as fusion with bones implanted at a front of a disk, thereby resulting in an excellent bone fusion. According to one embodiment of the present invention, there is provided a cage for spinal interbody fusion including: a cage body; and a tip part formed by extending from the cage body with a predetermined curvature, wherein the cage body includes: a cavity part formed by penetrating from a top surface to a bottom surface of the cage body; projection parts having a plurality of projections formed on the top surface and the bottom surface; and at least one perforation part which is perforated from a side surface adjacent to the top surface or the bottom surface toward the cavity part, and is located in the anterior direction of the cavity part.

Advantageous Effects

According to one embodiment of the present invention, there is a first effect that, since the tip part of the cage body is formed in a shape having a curvature larger than the curvature of a hemisphere, a phenomenon in which the cage body is locked to the vertebra does not occur at the time of insertion of the cage, and a fusion effect with the bones implanted at the front of the disk through the perforation part adjacent to the tip part may be expected, such that the bones can be quickly and stably fused with each other.

According to another embodiment of the present invention, there is a second effect that, since the inner surfaces of portions which are perforated in a predetermined shape at the side surfaces of the cage are not formed perpendicularly to the outer surface, the bones can be quickly fused with each other with sufficient durability.

It should be understood that the effects of the present invention are not particularly limited to those described above, and the present invention includes all effects that can be deduced from the detailed description of the invention or the configurations of the invention described in the claims.

DESCRIPTION OF DRAWINGS

FIGS. 5A and B are a top view and a side view of the cage for spinal interbody fusion according to the embodiment of the present invention, respectively.

FIGS. 6A and B are a front view and a rear view of the cage for spinal interbody fusion according to the embodiment of the present invention, respectively.

BEST MODE

In order to achieve the above-described technical objects, according to one embodiment of the present invention, there is provided a cage for spinal interbody fusion including: a cage body; and a tip part formed by extending from the cage body with a predetermined curvature, wherein the cage body includes: a cavity part formed by penetrating from a top surface to a bottom surface of the cage body; projection parts having a plurality of projections formed on the top surface and the bottom surface; and at least one perforation part which is perforated from a side surface adjacent to the top surface or the bottom surface toward the cavity part, and is located in the anterior direction of the cavity part.

In an embodiment of the present invention, the tip part may have a streamlined groove formed in at least a portion thereof.

In the embodiment of the present invention, the perforation part may be formed across the cage body and the tip part.

In the embodiment of the present invention, the perforation part may be formed in an ellipse shape.

In the embodiment of the present invention, the perforation part may have an inner surface slantly formed so as to be decreased toward an inside from an outside thereof.

In the embodiment of the present invention, the tip part may have a curvature value which is larger than a first curvature value (a curvature value when the tip part has a hemispherical shape) and is smaller than a second curvature value (a half (½) of the curvature value when the tip part has the hemispherical shape).

In the embodiment of the present invention, the cage for spinal interbody fusion may further include a connection part which is connected with an insertion rod.

In the embodiment of the present invention, the cage for spinal interbody fusion may further include at least one insertion hole formed at a predetermined position thereof, into which a marker made of a metal material to determine the installation position of the cage body is inserted.

In the embodiment of the present invention, the cage for spinal interbody fusion may further include at least one marker and insertion hole formed at predetermined positions of the tip part.

In the embodiment of the present invention, the cage body and the tip part may be made of a titanium (Ti) alloy material containing one or two metals selected from a group consisting of cobalt (Co) and chromium (Cr).

In the embodiment of the present invention, the cage body may be made of a material further containing a radiolucency material that allows an installation position of the cage body to be determined.

In the embodiment of the present invention, all or a part of the cage body and the tip part may be formed in a porous structure, respectively.

MODE FOR INVENTION

Hereinafter, the present invention will be described with reference to the accompanying drawings. However, the present invention may be realized in various forms, and it is not limited to the embodiments described herein. In the drawings, publicly known functions and configurations that are judged to be able to make the purport of the present invention unnecessarily obscure will not be illustrated. Referring to the drawings, wherein like reference characters designate like or corresponding parts throughout the several views.

Throughout this specification, when it is described that an element is "connected (bonded, contacted, and coupled)" to another element, the element may be "directly connected" to the other element or "indirectly connected" with the other element interposed therebetween. Throughout the specification and the claims, unless explicitly described to the contrary, the word "comprise" and variations such as "comprises" or "comprising" will be understood to imply the inclusion of stated elements but not the exclusion of any other elements.

Terms used in the present application are used only to describe specific embodiments, and are not intended to limit the present invention. Singular expressions used herein include plural expressions unless they have definitely opposite meanings in the context. In the present application, it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

Hereinafter, an embodiment of the present invention will be described in detail with reference to the accompanying drawings.

Figure 1:
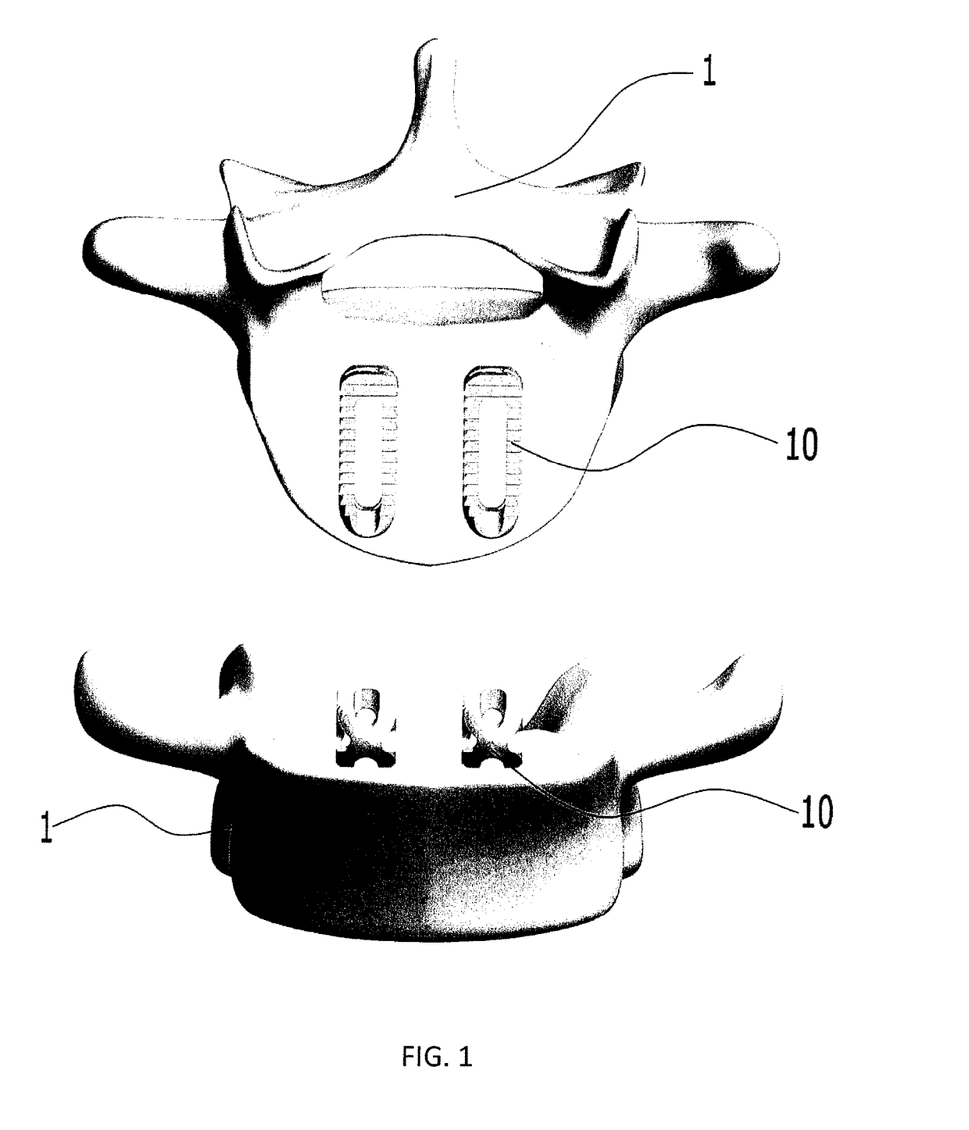
FIG. 1 is a view illustrating an example of a cage for spinal interbody fusion according to an embodiment of the present invention.

FIG. 1 is a view illustrating an example of a cage for spinal interbody fusion 10 according to the embodiment of the present invention.

As illustrated in FIG. 1, the cage for spinal interbody fusion 10 is inserted between vertebrae 1 to constantly maintain a space corresponding to an intervertebral disk, and allows bone chips or bone substitutes such as an artificial bone or autogenous bone filled in the internal space thereof and the adjacent vertebra 1 to be fused with each other.

Hereinafter, as used herein, the term "anterior" refers to a front side in terms of a patient, and the term "posterior" refers to a rear side in terms of the patient.

Figure 2:
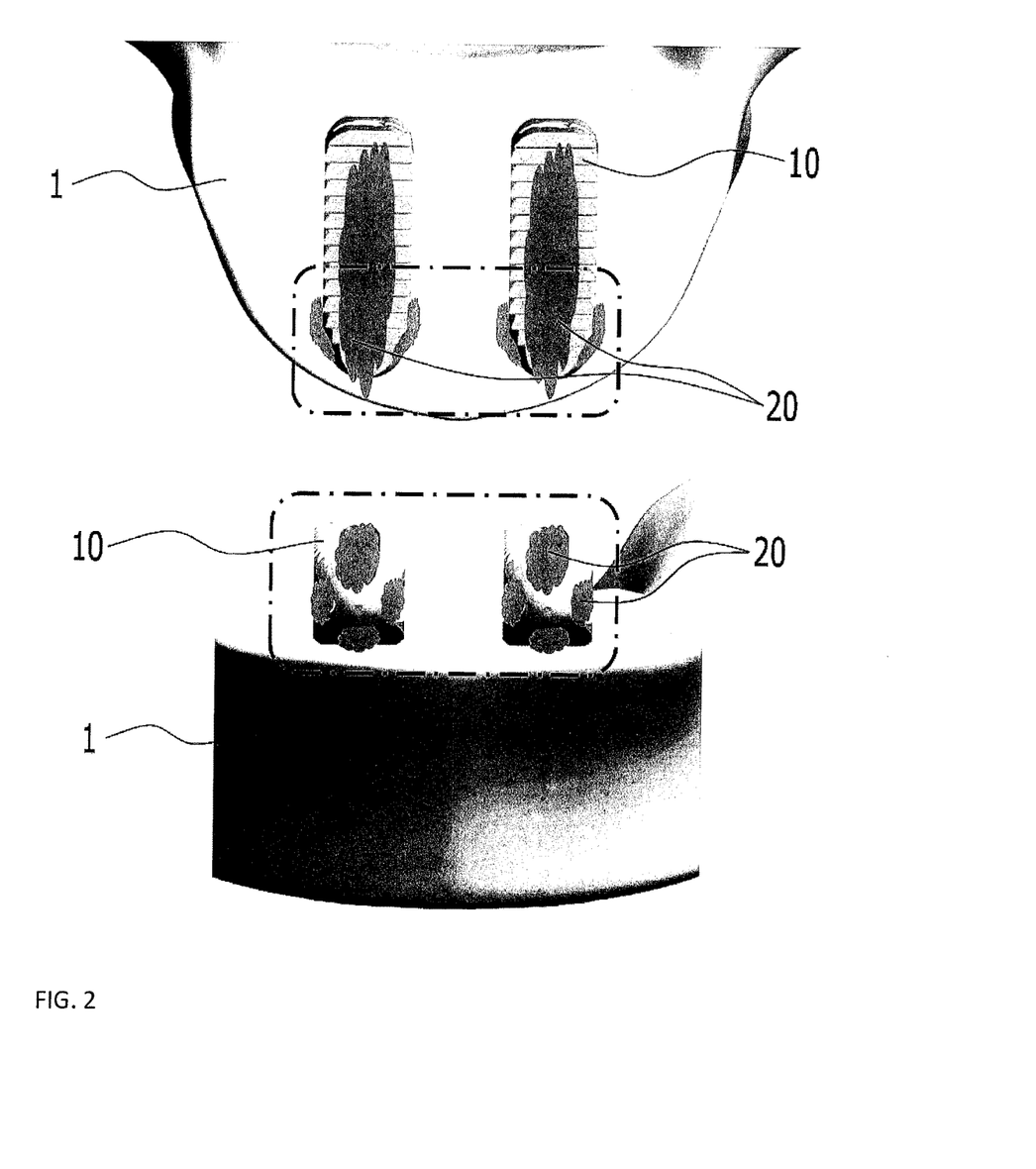
FIG. 2 is a view illustrating a state in which, in the cage for spinal interbody fusion according to the embodiment of the present invention, bone chips or bone substitutes (one-dot chain line) such as an artificial bone or autogenous bone implanted in the anterior region are in contact with an anterior cavity part, a perforation part and a groove of a cage for spinal interbody fusion 10.

FIG. 2 is a view illustrating a state in which, in the cage for spinal interbody fusion 10 according to the embodiment of the present invention, the bone chips or bone substitutes (one-dot chain line), such as an artificial bone or autogenous bone implanted in the anterior region, are in contact with an anterior cavity part 130, perforation parts 300 and a groove 210 of the cage for spinal interbody fusion 10.

In FIG. 2, a portion indicated by the one-dot chain line illustrates a region in which the bone chips or bone substitutes such as an artificial bone or autogenous bone implanted in an anterior direction are located between the vertebrae 1 (hereinafter referred to as an "anterior region").

FIG. 2 illustrates only the bone chips or bone substitutes such as an artificial bone or autogenous bone filled in the cage for spinal interbody fusion 10 except for the vertebrae or implanted bones of the anterior region for better understanding. In fact, the implanted bone, and the like may be present in the anterior region around the cage for spinal interbody fusion 10.

As illustrated in FIG. 2, the bone chips or bone substitutes 20 such as an artificial bone or autogenous bone injected into the perforation parts 300 and the groove 210 of the anterior region may be concentrically exposed at the anterior position, to cause the vertebrae or implanted bones of the anterior region to be rapidly and stably fused with each other.

Figure 3:
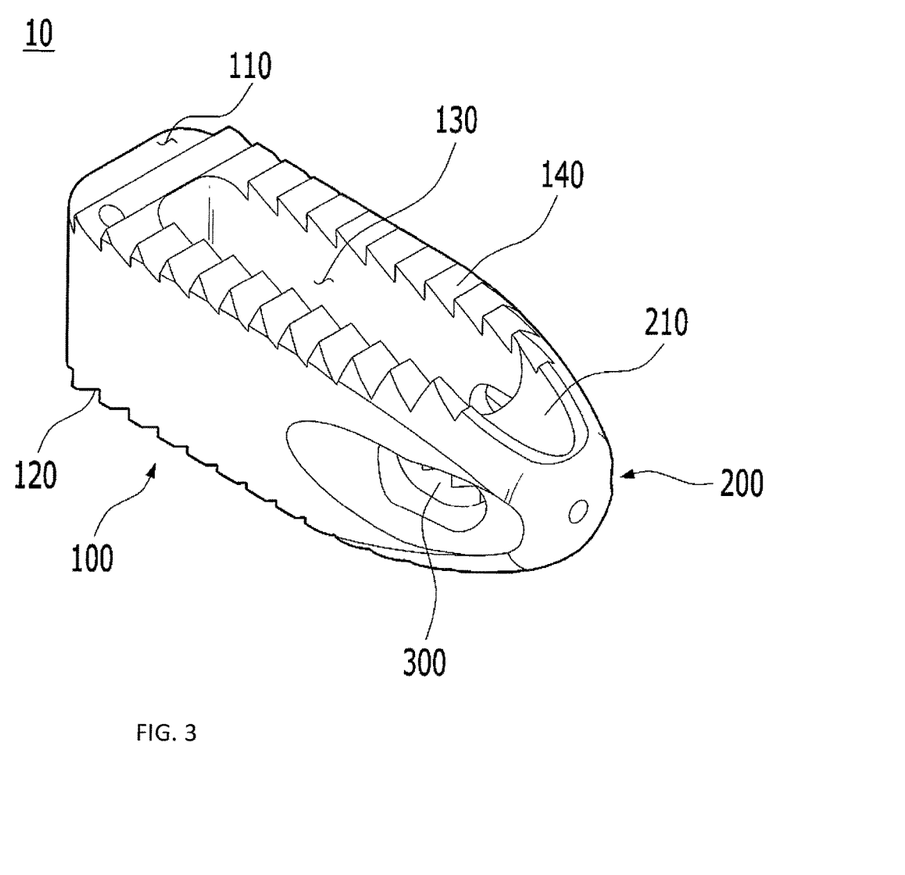
FIG. 3 is a perspective view of the cage for spinal interbody fusion according to the embodiment of the present invention.

FIG. 3 is a perspective view of the cage for spinal interbody fusion 10 according to the embodiment of the present invention.

As illustrated in FIG. 3, the cage for spinal interbody fusion includes a cage body 100, and a tip part 200 formed by extending from the cage body 100 with a predetermined curvature. The cage body 100 may include the cavity part 130 formed by penetrating from a top surface 110 to a bottom surface 120 of the cage body 100, projection parts 140 having a plurality of projections formed on the top surface 110 and the bottom surface 120, and at least one perforation part 300 which is perforated from a side surface adjacent to the top surface 110 or the bottom surface 120 toward the cavity part 130, and is located in the anterior direction of the cavity part 130.

The top surface 110 of the cage body 100 may be provided on a side closest to a head of a patient, and the bottom surface 120 of the cage body 100 may be provided on a side closest to feet of the patient.

The tip part 200 may have a streamlined groove 210 formed in at least a portion thereof.

The tip part 200 may be formed forward in a direction in which the cage for spinal interbody fusion 10 is inserted.

When the tip part 200 has the streamlined groove formed therein, the bone chips or bone substitutes such as an artificial bone or autogenous bone filled therein may be easily exposed in the front of the tip part 200, and allow the bone to be quickly and stably grown by improving a bone density during being fused with the bones implanted in the anterior region.

The tip part 200 has a hole formed in a shape communicating with the cavity part 130 and the perforation parts 300, and may serve to increase an exposed surface area of the bone chip or bone substitute such as an artificial bone or autogenous bone.

The perforation part 300 may be formed across the cage body 100 and the tip part 200.

The perforation part 300 may be formed only in the tip part 200 provided in the anterior direction, or only in the side surface of the cage body 100, and may be formed across the cage body 100 and the tip part 200.

Preferably, in order to increase the exposed area of the bone chip or bone substitute such as an artificial bone or autogenous bone, the perforation part may be formed across the cage body 100 and the tip part 200 in the anterior direction, while being formed to be biased to the tip part 200 so as to have an exposed area more concentrated in the anterior direction.

The perforation part 300 may include the groove 210 of the tip part 200 while being formed across the tip part 200 in the cage body 100. Thereby, the bone chips or bone substitutes such as an artificial bone or autogenous bone exposed through the perforation part 300 can be fused with each other between the vertebrae 1 adjacent to the tip part 200 with a high efficiency.

The perforation part 300 may be formed in an ellipse shape.

The perforation part 300 may have an inner surface slantly formed so as to be decreased toward an inside from an outside thereof.

When the inner surface of the perforation part 300 is slantly formed, it has a section on the anterior tip part 200 side which is steeply formed, and a section on the posterior cage body 100 corresponding thereto which is smoothly formed, such that the section of the perforation part 300 on the cage body 100 side may have a larger area exposed to the outside than the section of perforation part 300 on the tip part 200 side.

The perforation part 300 may be formed in the ellipse shape to increase the durability against a spinal load. In addition, even in the event of a strong momentary impact, the amount of impact may be quickly dispersed to the surroundings.

The perforation part 300 has the largest size on the outside and is decreased toward the inside, thereby maximizing the area in which the bone chip or bone substitute such as an artificial bone or autogenous bone is exposed to the outside while satisfying the durability required in the cage.

In the embodiment of the present invention, an example, in which the perforation part 300 is formed in the ellipse shape, has been described. However, it is not particularly limited thereto, and the perforation part 300 may be formed in a polygonal shape capable of rapidly dispersing the amount of impact.

Also, in the embodiment of the present invention, an example, in which two perforation parts 300 are formed on both sides of the cage body, has been described. However, it is not particularly limited thereto, and a plurality of perforation parts 300 exceeding two may be formed.

The tip part 200 may have a curvature value which is larger than a first curvature value (a curvature value when the tip part 200 has a hemispherical shape) and is smaller than a second curvature value (a half (½) of the curvature value when the tip part 200 has the hemispherical shape).

When the tip part 200 has a curvature value larger than the first curvature value, the cage for spinal interbody fusion 10 may be easily inserted, and the area of the bone chip or bone substitute such as an artificial bone or autogenous bone exposed through the groove 210 may be increased. In most of the conventional cage bodies, an anterior part corresponding to the tip part 200 of the present invention is formed in a hemispherical or planar shape, such that a phenomenon in which the cage body is locked to the vertebra may occur at the time of insertion of the cage, and is designed to allow the vertebrae to be fused with each other. Further, since the anterior part of the conventional cage body has an unpenetrated structure, it is difficult to be fused with the bones implanted in the anterior region, thereby resulting in an unstable structure.

When the tip part 200 has a curvature value smaller than the second curvature value, it may have the durability required in the cage.

In the embodiment of the present invention, the bone chip or bone substitute such as an artificial bone or autogenous bone filled in the cage for spinal interbody fusion 10 has an area of 11 mm$^2$ by the groove 210, 69 mm$^2$ by the perforation part 300 including the groove 210, and 205 mm$^2$ by the cavity part 130, such that it may be exposed to a space between the vertebrae 1 with a total area of 285 mm².

The cage body 100 and the tip part 200 may be made of a titanium (Ti) alloy material containing one or two metals selected from a group consisting of cobalt (Co) and chromium (Cr).

The cage body 100 and the tip part 200 may be made of polyetheretherketone (PEEK).

In addition, the cage body 100 and the tip part 200 may also be made of a biocompatible material selected from a group consisting of carbon fibers, carbon polymers or other polymers, various metals, memory metals, ceramics, bones, bio-resorbable composites, and a composition thereof.

The cage body 100 may be made of a material further containing a radiolucency material that allows for an installation position of the cage body 100 to be determined.

The cage body 100 may contain a radiolucency material to facilitate determination of a position thereof when it is covered or exposed to X-rays. The radiolucency material may be contained in the material forming the cage body 100 or may be applied to an outer surface of the cage body 100.

All or a part of the cage body 100 and the tip part 200 may be formed in a porous structure, respectively.

When all or a part of the cage body 100 and the tip part 200 are formed in a porous structure, respectively, the exposed area of the bone chip or bone substitute such as an artificial bone or autogenous bone filled therein may be increased, so as to be quickly and stably fused with the bone-grown vertebra 1. Such a porous structure may be any one selected from a group consisting of triangular, square, pentagonal, hexagonal, octagonal, and circular structures.

Figure 4:
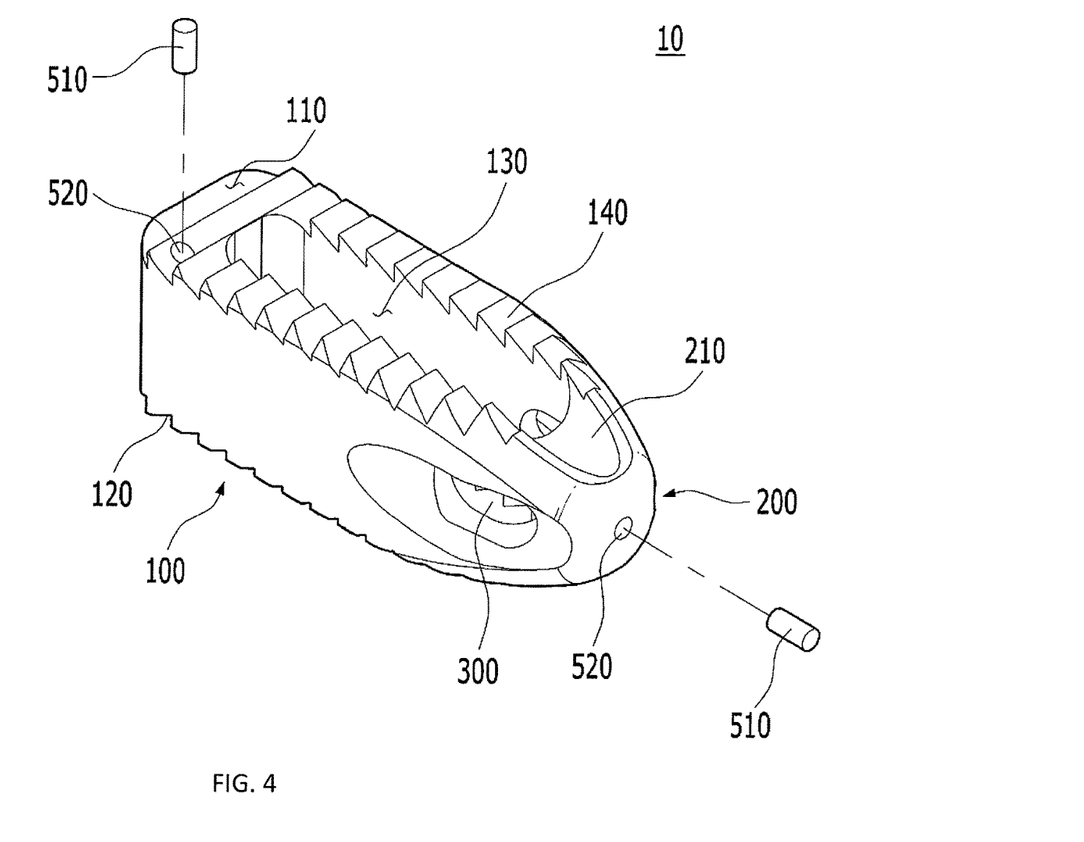
FIG. 4 is a perspective view of the cage for spinal interbody fusion in which a marker is separated therefrom according to the embodiment of the present invention.

FIG. 4 is a perspective view of the cage for spinal interbody fusion 10 according to the embodiment of the present invention in which a marker 510 is separated therefrom.

As illustrated in FIG. 4, the cage body 100 may have at least one insertion hole 520 formed at a predetermined position thereof, and a marker 510 made of a metal material for determining the installation position of the cage body 100 is inserted into the insertion hole.

The cage body may further include at least one marker 510 and insertion hole 520 formed at predetermined positions of the tip part 200.

The marker 510 may have a function of allowing an operator to easily determine the position of the cage for spinal interbody fusion 10 at the time of X-ray imaging or the like.

The marker 510 may be located at an edge of the cage body 100 and at a center of the tip part 200. The marker 510 of the cage body 100 is inserted in a vertical direction, while the marker 510 of the tip part 200 is inserted in a horizontal direction, so that the position of the cage may be more easily determined at the time of X-ray imaging or the like.

In the embodiment of the present invention, an example, in which the pin-shaped marker 510 is inserted into the insertion hole 520, has been described, but it is not particularly limited thereto, and the marker may have a shape other than the pin, or may be integrally formed with the cage body 100 or the tip part 200, and may not be the type to be inserted into the insertion hole 520.

Figure 5:
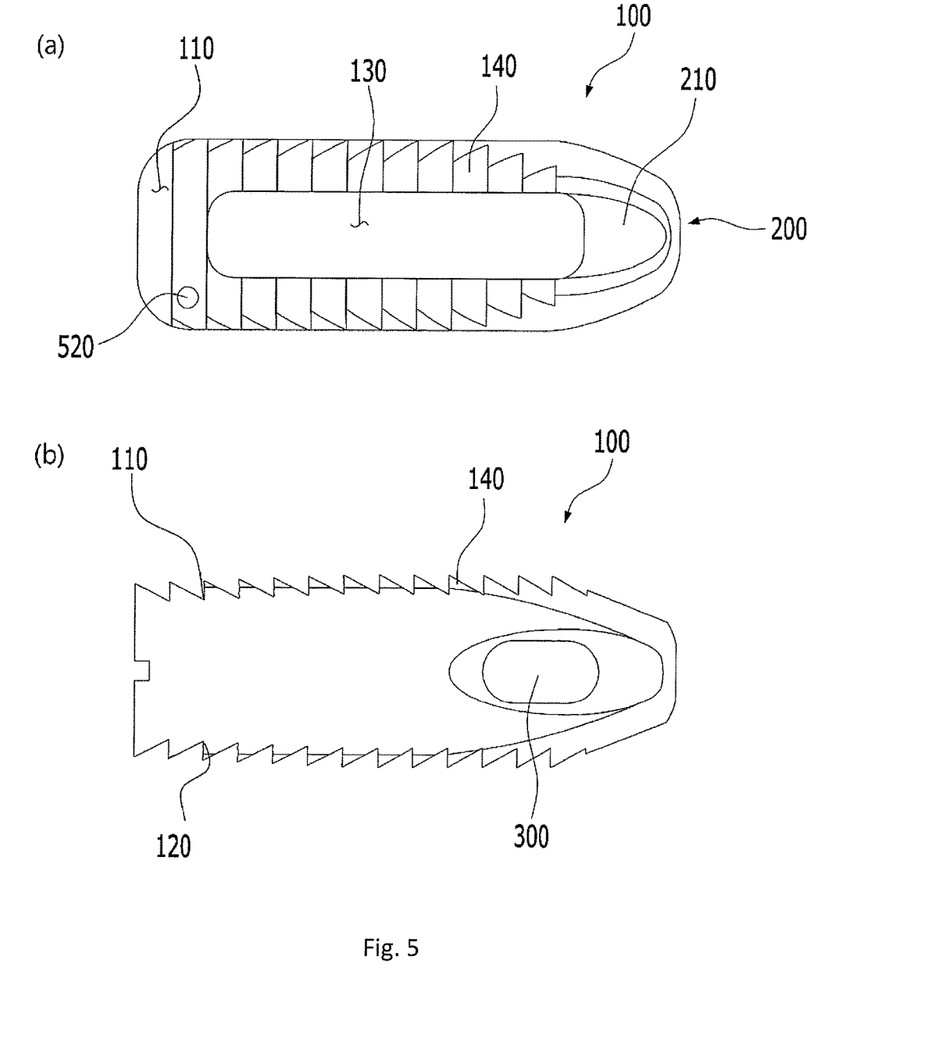

FIG. 5 is a top view and a side view of the cage for spinal interbody fusion 10 according to the embodiment of the present invention. Specifically, FIG. 5A is a plan view of the cage for spinal interbody fusion 10, and FIG. 5B is a side view of the cage for spinal interbody fusion 10.

As illustrated in FIGS. 5A and 5B, the projection parts 140 having the plurality of projections are formed on the top surface 110 and the bottom surface 120 of the cage body 100.

The projection parts 140 allow the cage for spinal interbody fusion 10 to be fixed without being retracted when it is inserted between the vertebrae 1 and then separated from a surgical insertion rod, and be maintained at the initial inserted position even during being fused.

The projections of the projection part 140 may have a wedge shape which is inclined in a direction opposite to a direction in which the cage body 100 is inserted between the vertebrae 1, so that the cage can be easily inserted between the vertebrae 1.

In the embodiment of the present invention, an example, in which the projection part 140 has an inclined wedge shape, has been described, but it is not particularly limited thereto, and it may have a shape that can prevent the cage from being retracted and fix thereto such as a thread shape or a hook shape.

Figure 6:
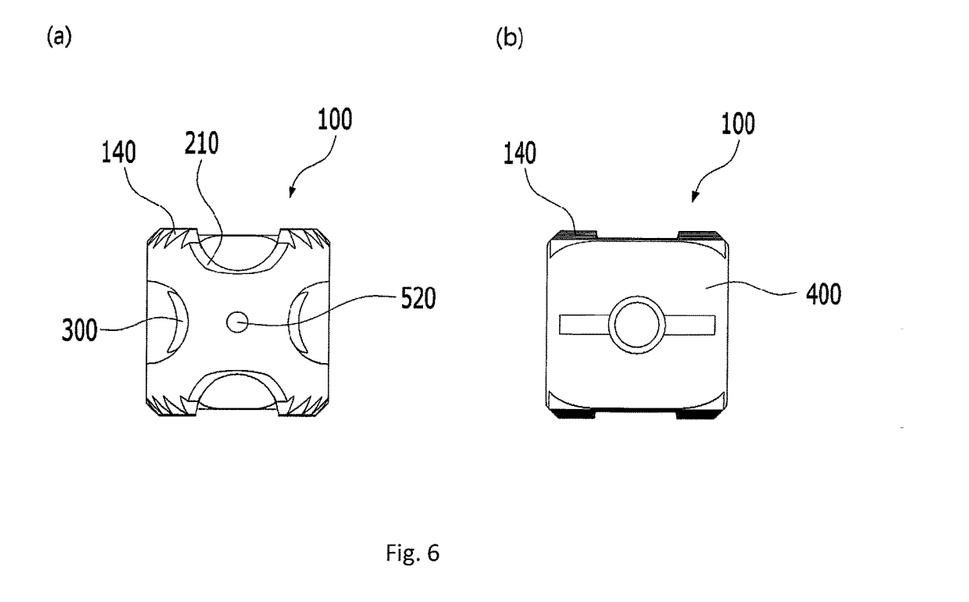

FIG. 6 is a front view and a rear view of the cage for spinal interbody fusion 10 according to the embodiment of the present invention. Specifically, FIG. 6A is a front view of the cage for spinal interbody fusion 10, and FIG. 6B is a rear view of the cage for spinal interbody fusion 10.

As illustrated in FIG. 6A, in the embodiment of the present invention, an example, in which the cage for spinal interbody fusion 10 has a rectangular shape when viewing it from the front, has been described, but it is not particularly limited thereto, and it may be formed in a curved surface at the side surface.

As illustrated in FIG. 6B, the cage for spinal interbody fusion 10 may further include a connection part 400 which is connected with the insertion rod.

The connection part 400 may be formed at the rear end portion of the cage body 100, and may have a hole at the center thereof to which the insertion rod can be coupled. Herein, the hole to which the insertion rod is coupled may be provided with a female screw formed thereon, and may be screwed with a male thread formed at an end of the insertion rod when inserting the cage for spinal interbody fusion 10 between the vertebrae 1.

TABLE 1

| Sample | Test item | 1 | 2 | 3 | 4 | 5 | 6 | Avg. |
|---|---|---|---|---|---|---|---|---|
| Cage for anterior spinal interbody fusion | Yield displacement (mm) | 0.93 | 1.49 | 1.93 | 1.49 | 1.93 | 1.45 | 1.54 |
| | Yield load (N) | 6,861 | 9,734 | 8,476 | 9,738 | 8,477 | 9,667 | 8,826 |
| | Stiffness (N/mm) | 7,314 | 7,788 | 12,321 | 8,029 | 7,142 | 8,045 | 8,440 |

TABLE 1-continued

| Sample | Test item | 1 | 2 | 3 | 4 | 5 | 6 | Avg. |
|---|---|---|---|---|---|---|---|---|
| | Max. displacement (mm) | 1.99 | 2.21 | 2.72 | 2.21 | 2.72 | 2.16 | 2.34 |
| | Max. load (N) | 13,017 | 13,474 | 11,980 | 13,475 | 11,978 | 13,388 | 12,885 |

The above Table 1 illustrates test results of a mechanical strength of the cage for spinal interbody fusion according to the embodiment of the present invention.

As shown in Table 1, the cage for anterior spinal interbody fusion may have an average (avg.) yield displacement value of 1.54 mm, an average (avg.) yield load value of 8,826 N, and an average (avg.) stiffness value of 8,440 N/mm, as well as may have an average (avg.) maximum displacement value of 2.34 mm, and an average (avg.) maximum load (max. load) value of 12,885 N.

The yield load of test item 1 in Table 1 is 6,861 N, which may be the smallest of the test result values for the yield load. This value may resist a 700 kg load (700 Kg×9.8 m/s=6,860 N). Thus, considering the vertebrae that can withstand an upper body load of a person, the cage for spinal interbody fusion 10 may have the required durability.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implanted in a distributed manner. Likewise, components described to be distributed can be implanted in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

The invention claimed is:

1. A cage for spinal interbody fusion comprising:
   a cage body; and
   a tip part formed by extending from the cage body with a predetermined curvature,
   wherein the cage body comprises:
      a cavity part formed by penetrating from a top surface to a bottom surface of the cage body;
      projection parts having a plurality of projections formed on the top surface and the bottom surface; and
      at least one perforation part which is perforated from a side surface adjacent to the top surface or the bottom surface toward the cavity part, and is located in an anterior direction of the cavity part;
   wherein the tip part includes a concavely curved groove formed in an upper portion thereof being recessed in a concave curved shape with a predetermined depth, and has a form continued to the cavity part and the perforation part, thus to increase an exposed surface area of a bone chip or bone substitute such as an artificial bone or autogenous bone; and
   the perforation part is formed so as to have a larger inclination in an anterior direction continued to the tip part than an inclination in a posterior direction continued to the cage body, and has an inner surface which is formed by sloping so as to be decreased a cross section of the perforation part toward an inside from an outside thereof, thus to satisfy durability and increase an exposed surface area of the bone chip or bone substitute such as an artificial bone or autogenous bone.

2. The cage for spinal interbody fusion according to claim 1, wherein the perforation part is formed across the cage body and the tip part.

3. The cage for spinal interbody fusion according to claim 2, wherein the perforation part is formed in an ellipse shape.

4. The cage for spinal interbody fusion according to claim 1, wherein the tip part has a curvature value which is larger than a first curvature value and smaller than a second curvature value, and wherein the second curvature value is one-half of the first curvature value when the tip part has a hemispherical shape.

5. The cage for spinal interbody fusion according to claim 1, further comprising a connection part connected to an insertion rod.

6. The cage for spinal interbody fusion according to claim 1, further comprising at least one insertion hole formed at a predetermined position of the cage body, and a marker inserted into the at least one insertion hole that is made of a metal material, whereby the installation position of the cage body can be identified.

7. The cage for spinal interbody fusion according to claim 6, further comprising at least one insertion hole formed at predetermined position of the tip part, and a marker inserted into the at least one insertion hole of the tip part that is made of a metal material, whereby the installation position of the tip part can be identified.

8. The cage for spinal interbody fusion according to claim 1, wherein the cage body and the tip part are made of a titanium (Ti) alloy material containing one or two metals selected from a group consisting of cobalt (Co) and chromium (Cr).

9. The cage for spinal interbody fusion according to claim 8, wherein the cage body is made of a material further containing a radiolucent material that allows an installation position of the cage body to be determined.

10. The cage for spinal interbody fusion according to claim 1, wherein all or a part of the cage body and the tip part are formed as porous structures.

* * * * *